United States Patent
Stadler et al.

(10) Patent No.: US 7,103,404 B2
(45) Date of Patent: Sep. 5, 2006

(54) DETECTION OF TACHYARRHYTHMIA TERMINATION

(75) Inventors: Robert W. Stadler, Shoreview, MN (US); Eduardo N. Warman, Maple Grove, MN (US); James H. Ericksen, North Oaks, MN (US); Reece W. Holbrook, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 516 days.

(21) Appl. No.: 10/375,457

(22) Filed: Feb. 27, 2003

(65) Prior Publication Data

US 2004/0171959 A1 Sep. 2, 2004

(51) Int. Cl.
*A61B 5/0452* (2006.01)
*A61N 1/37* (2006.01)

(52) U.S. Cl. ............... 600/515; 600/509; 600/518; 600/519; 607/14; 607/18

(58) Field of Classification Search ........ 600/515–519; 607/14

See application file for complete search history.

(56) References Cited

U.S. PATENT DOCUMENTS

| | | | |
|---|---|---|---|
| 4,830,006 A * | 5/1989 | Haluska et al. | 607/4 |
| 4,949,719 A * | 8/1990 | Pless et al. | 607/7 |
| 5,193,536 A | 3/1993 | Mehra | |
| 5,240,009 A | 8/1993 | Williams | |
| 5,312,441 A * | 5/1994 | Mader et al. | 607/5 |
| 5,342,402 A | 8/1994 | Olson et al. | |
| 5,400,795 A | 3/1995 | Murphy et al. | |
| 5,730,141 A | 3/1998 | Fain et al. | |
| 5,779,645 A * | 7/1998 | Olson et al. | 600/518 |
| 5,941,831 A * | 8/1999 | Turcott | 600/515 |
| 6,078,837 A | 6/2000 | Peterson et al. | 607/14 |
| 6,169,923 B1 * | 1/2001 | Kroll | 607/5 |
| 6,178,350 B1 | 1/2001 | Olson et al. | |
| 6,393,316 B1 | 5/2002 | Gillberg et al. | 600/515 |
| 6,430,435 B1 | 8/2002 | Hsu et al. | |
| 6,636,764 B1 * | 10/2003 | Fain et al. | 607/5 |
| 2002/0058958 A1 | 5/2002 | Sun et al. | 607/14 |

FOREIGN PATENT DOCUMENTS

WO  WO 2004/050181 A1  6/2004

* cited by examiner

*Primary Examiner*—Robert Pezzuto
*Assistant Examiner*—Yun Haeng Lee
(74) *Attorney, Agent, or Firm*—Michael C. Soldner; Girma Wolde-Michael

(57) ABSTRACT

Determining termination of an identified tachyarrhythmia episode may involve analysis of a relative decrease in tachyarrhythmia rate, a normalization of electrogram morphology criteria, or both. An implanted medical device may obtain a tachyarrhythmia rate and a morphology of a cardiac waveform. The device may compare the tachyarrhythmia rate to a threshold tachyarrhythmia rate and the morphology to a template morphology, and classify the heart beat as indicating termination of the tachyarrhythmia episode when the tachyarrhythmia rate is less than the threshold tachyarrhythmia rate, the morphology categorizes as normal, or both. For arrhythmias with no therapy delivered, observation of arrhythmia behavior at the point of termination may lead to improved classification. In addition, observation of a relative decrease in tachyarrhythmia rate immediately after therapy application can lead to application of slower but more specific criteria for redetection. Also, delivery of cardioversion shocks can be aborted upon tachyarrhythmia termination.

34 Claims, 8 Drawing Sheets

DETECTION OF TACHYARRHYTHMIA TERMINATION

TECHNICAL FIELD

The invention relates to cardiac pacing systems and, more particularly, to systems for delivering pacing therapies to treat tachyarrhythmia.

BACKGROUND

An arrhythmia is a disturbance in the normal rate, rhythm or conduction of the heartbeat. A tachyarrhythmia is a condition in which an arrhythmia is occurring at a high rate, e.g., 100 or more beats per minute. Arrhythmias may be classified broadly by the chamber of the heart in which the arrhythmia originates. Such classification includes supraventricular tachycardia, ventricular tachycardia, or concomitant supraventricular and ventricular tachycardia, defined here as "double tachycardia." Tachycardias can lead to fibrillation, which is characterized by a chaotic activation of myocardial tissue. Ventricular tachycardia and ventricular fibrillation can be life threatening over a period of minutes.

Treatment for tachyarrhythmias may include anti-tachycardia pacing (ATP), cardioversion, or defibrillation in which a train of high rate pulses or one or more high-energy pulses is delivered to the heart in an attempt to restore a more normal rhythm. ATP is typically effective in converting stable tachyarrhythmias to normal rhythm, and is often delivered via an implanted device. In some cases, a sequence of increasingly aggressive ATP therapies are applied until an episode of tachyarrhythmia is terminated. Some implanted devices can be configured to discontinue ATP and immediately apply cardioversion in the event the tachyarrhythmia degrades into fibrillation.

SUMMARY

In general, the invention is directed to techniques for determining whether an identified tachyarrhythmia episode has terminated. In other words, following identification of a tachyarrhythmia episode, the techniques continue to analyze the cardiac activity to determine whether the episode has terminated. The techniques may determine whether the tachyarrhythmia episode has terminated based on a relative decrease in tachyarrhythmia rate, a normalization of electrogram morphology criteria, or a combination thereof.

An implanted medical device, for example, can be configured to obtain both a tachyarrhythmia rate and a morphology of a cardiac waveform. The implanted medical device uses the obtained tachyarrhythmia rate and morphology to determine whether the heart beat indicates termination of the identified tachyarrhythmia episode. The tachyarrhythmia may be atrial or ventricular.

According to some embodiments, a processor compares the tachyarrhythmia rate to a relative threshold rate and compares the morphology to a template morphology. The processor classifies the beat as indicating termination of the tachyarrhythmia episode when the tachyarrhythmia rate drops below the relative threshold rate and the morphology of the cardiac waveform substantially matches the template morphology. In some embodiments, the processor may determine that the tachyarrhythmia episode has terminated when a threshold number of successive beats are found to indicate termination of the tachyarrhythmia episode.

Upon determining that the tachyarrhythmia episode has spontaneously terminated, the processor may reclassify the episode by monitoring atrial and ventricular events immediately prior to deceleration of the tachyarrhythmia rate. In other words, the processor may verify, for example, whether the identified episode was truly a ventricular tachycardia or whether the episode was incorrectly identified. For example, when an atrial event is the last event prior to the deceleration, the processor classifies the tachyarrhythmia episode as a ventricular tachycardia. When a ventricular event is the last event prior to the deceleration, however, the processor classifies the tachyarrhythmia as a supraventricular tachycardia The processor may be configured to store information about the tachyarrhythmia episode, such as a type of tachyarrhythmia episode, a relative threshold rate, atrial and ventricular events captured during the tachyarrhythmia episode, and electrogram morphologies obtained during the tachyarrhythmia episode. When termination of the tachyarrhythmia is identified, the processor may reclassify the episode, thereby providing appropriate use of the memory resources. In addition, the processor may use the information obtained at termination to reclassify the stored information according to whether a ventricular tachycardia or a supraventricular tachycardia is detected.

The processor also may be configured to selectively deliver therapy in accordance with the tachyarrhythmia rate and morphology. For example, if the implanted medical device is programmed to deliver a cardioversion shock in the case of ventricular tachycardia, the processor may determine whether the identified tachyarrhythmia episode has terminated during a period of charging of capacitors or a confirmation period and, if so, forego the cardioversion shock. This feature can conserve battery resources and avoid painful, unnecessary therapies.

The processor may also be configured to observe changes in the tachyarrhythmia rate immediately after delivery of a therapy relative to the tachyarrhythmia rate immediately before delivery of a therapy. Based upon the detected change in tachyarrhythmia rate, the device may either proceed rapidly to a more aggressive therapy, proceed rapidly to the next sequence of programmed therapy, or proceed more slowly by taking time to re-analyze the rhythm to determine the appropriateness of additional therapies.

In one embodiment, the invention provides a method comprising obtaining a tachyarrhythmia rate associated with a heart beat, obtaining a morphology of a cardiac waveform associated with the tachyarrhythmia, and determining whether a detected tachyarrhythmia episode has terminated based on the tachyarrhythmia rate and the morphology.

In another embodiment, the invention provides a device comprising a first detector to detect a tachyarrhythmia rate associated with a heart beat, a second detector to detect a morphology of a cardiac waveform associated with the tachyarrhythmia, and a processor to determine whether a detected tachyarrhythmia episode has terminated based on the tachyarrhythmia rate and the morphology.

In another embodiment, the invention provides a method comprising obtaining a morphology of a cardiac waveform associated with a tachyarrhythmia and determining whether a detected tachyarrhythmia episode has terminated based on the morphology.

In another embodiment, the invention provides a method comprising measuring a metric of a tachyarrhythmia rate of a tachyarrhythmia episode upon detection of the tachyarrhythmia episode or later in the episode, calculating a relative threshold rate as a function of the metric of the rate of the tachyarrhythmia episode, comparing a tachyarrhythmia rate associated with a heart beat with the relative threshold rate, and determining whether the detected tachyarrhythmia episode has terminated based on the comparison.

The invention can provide a number of advantages. In general, the invention may be capable of more accurately determining whether an identified tachyarrhythmia episode has terminated. The tachyarrhythmia may be atrial or ventricular. Increased accuracy can be achieved by comparing a tachyarrhythmia rate with a relative threshold rate instead of an absolute threshold rate. In this manner, the threshold rate is relative to the particular tachyarrhythmia episode. Further, the accuracy and sensitivity of detected terminations may be improved by comparing a morphology of a cardiac waveform associated with the heart beat to a template morphology. For example, the criteria for categorizing a morphology as normal compared to the template may be adjusted to increase or decrease the sensitivity.

Improvements in the detection of arrhythmia termination may benefit three areas. First, for arrhythmias with no therapy delivered, observation of the behavior of the arrhythmia at the point of spontaneous termination may lead to improved arrhythmia classification. By determining how a tachyarrhythmia episode has terminated, the invention may permit more selective storage of episodic information, thereby conserving memory space. Further, selective storage of episodic information prevents filling up memory space with false detections. Second, the use of a relative tachyarrhythmia rate may aid in redetection of the tachyarrhythmia episode after applying therapy. In this manner, the invention leads to a determination of the urgency for applying subsequent therapies. For example, an observed slowing of the arrhythmia after a first therapy may lead to the application of slower and more specific criteria for redetection of the arrhythmia before application of a second therapy. Third, the invention may permit delivery of cardioversion shocks to be aborted upon tachyarrhythmia termination, thereby conserving battery resources, avoiding painful and unnecessary therapies, and extending device longevity.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
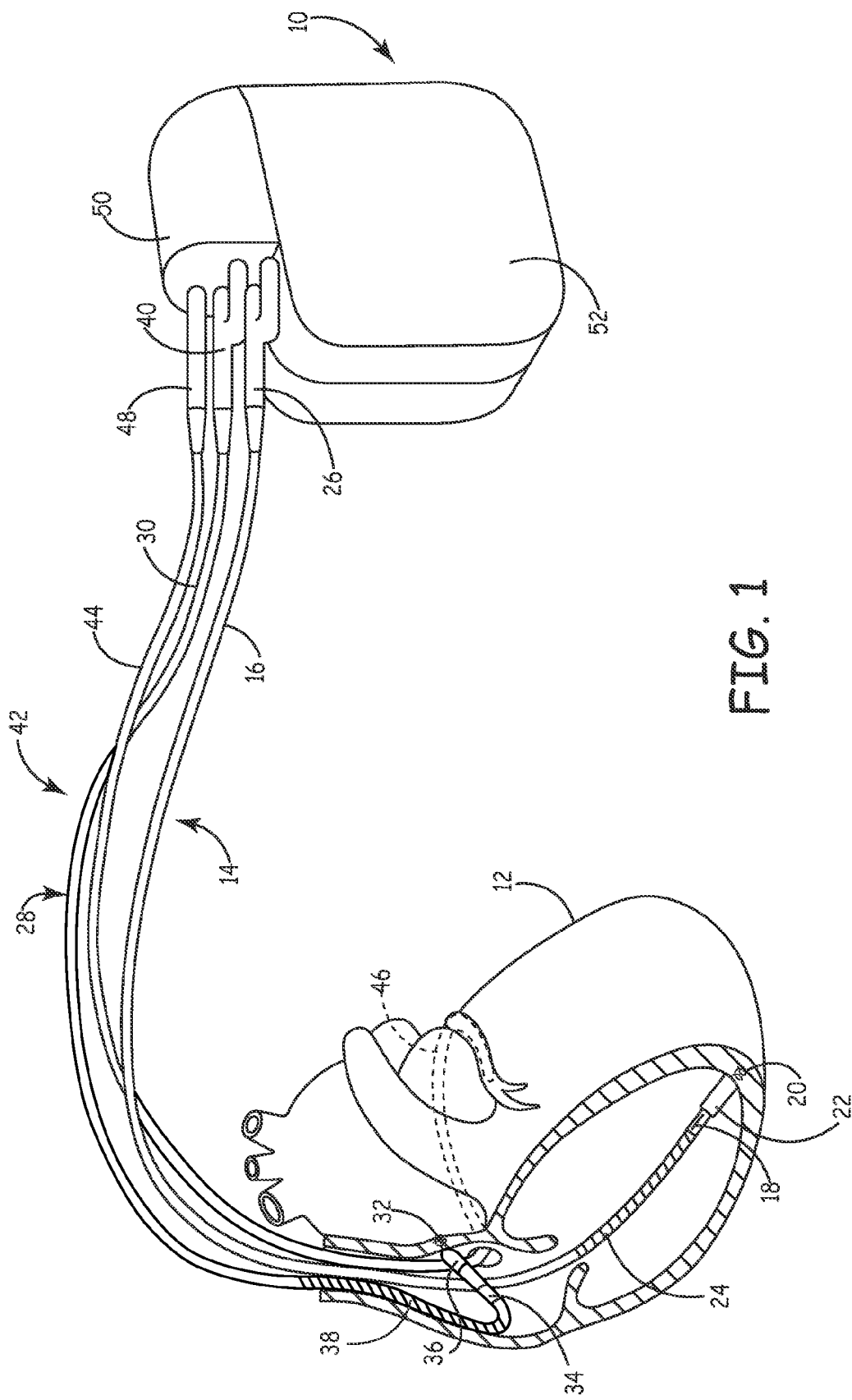
FIG. 1 is a diagram illustrating an implanted medical device useful in delivering anti-tachyarrhythmia therapies.

FIG. 1 is a diagram illustrating an implanted medical device 10 useful in delivering anti-tachyarrhythmia therapies. Device 10, shown in conjunction with a human heart 12, may be configured to deliver anti-tachycardia pacing (ATP) therapy as well as cardioversion and defibrillation shocks, and monitor the effect of the delivered therapy. As will be described, implanted medical device 10 can be configured to determine whether a tachyarrhythmia episode has terminated based on a relative decrease in tachyarrhythmia rate, a normalization of electrogram morphology criteria, or a combination thereof. For example, implanted medical device 10 may determine tachyarrhythmia termination based on both a relative decrease in tachyarrhythmia rate and application of electrogram morphology criteria. Implanted medical device 10 may adjust the delivered therapy or the criteria for redetection of arrhythmia after a therapy based on the determination, as well as abort cardioversion or defibrillation shocks. In addition, implanted medical device 10 may selectively store episodic information based on the determination, thereby conserving memory resources. The specific structure of device 10 is described below for purposes of example, and should not be considered limiting of the invention as broadly embodied herein.

As shown in FIG. 1, device 10 may include a ventricular lead 14 having an elongated insulative lead body 16, carrying three concentric coiled conductors, separated from one another by tubular insulative sheaths. Located adjacent the distal end of ventricular lead 14 are a ring electrode 18, an extendable helix electrode 20, mounted retractably within an insulative electrode head 22 and an elongated coil electrode 24. Each of electrodes 18, 20, and 24 is coupled to one of the coiled conductors within lead body 16. Electrodes 18, 20, and 24 can be used for both cardiac pacing and sensing of ventricular depolarizations, often referred to as ventricular events. At the proximal end of ventricular lead 14 is a bifurcated connector 26 that carries three electrical connectors, each coupled to one of the coiled conductors.

An atrial lead 28 includes an elongated insulative lead body 30, carrying three concentric coiled conductors, separated from one another by tubular insulative sheaths. Located adjacent the J-shaped distal end of atrial lead 28 are a ring electrode 32 and an extendable helix electrode 34, mounted retractably within an insulative electrode head 36 and an elongated coil electrode 38. Each of electrodes 32, 34, and 38 is coupled to one of the coiled conductors within lead body 30. Electrodes 32, 34, and 38 are employed for atrial pacing and for sensing atrial depolarizations, often referred to as atrial events. Elongated coil electrode 38 is provided proximal to ring electrode 32 and coupled to the third conductor within lead body 30. At the proximal end of lead 28 is a bifurcated connector 40 that carries three electrical connectors, each coupled to one of the coiled conductors.

A coronary sinus lead 42 includes an elongated insulative lead body 44, carrying one coiled conductor coupled to an elongated coiled defibrillation electrode 46. Electrode 46, illustrated in broken outline, is located within the coronary sinus and great vein of the heart. At the proximal end of lead 42 is a connector plug 48 that carries an electrical connector, coupled to the coiled conductor. Leads 14, 28, and 42 are inserted into a connector block 50 associated with device 10. Device 10 has an outer housing 52 that may function as a subcutaneous defibrillation electrode that defibrillates either the atria or ventricles.

Figure 2:
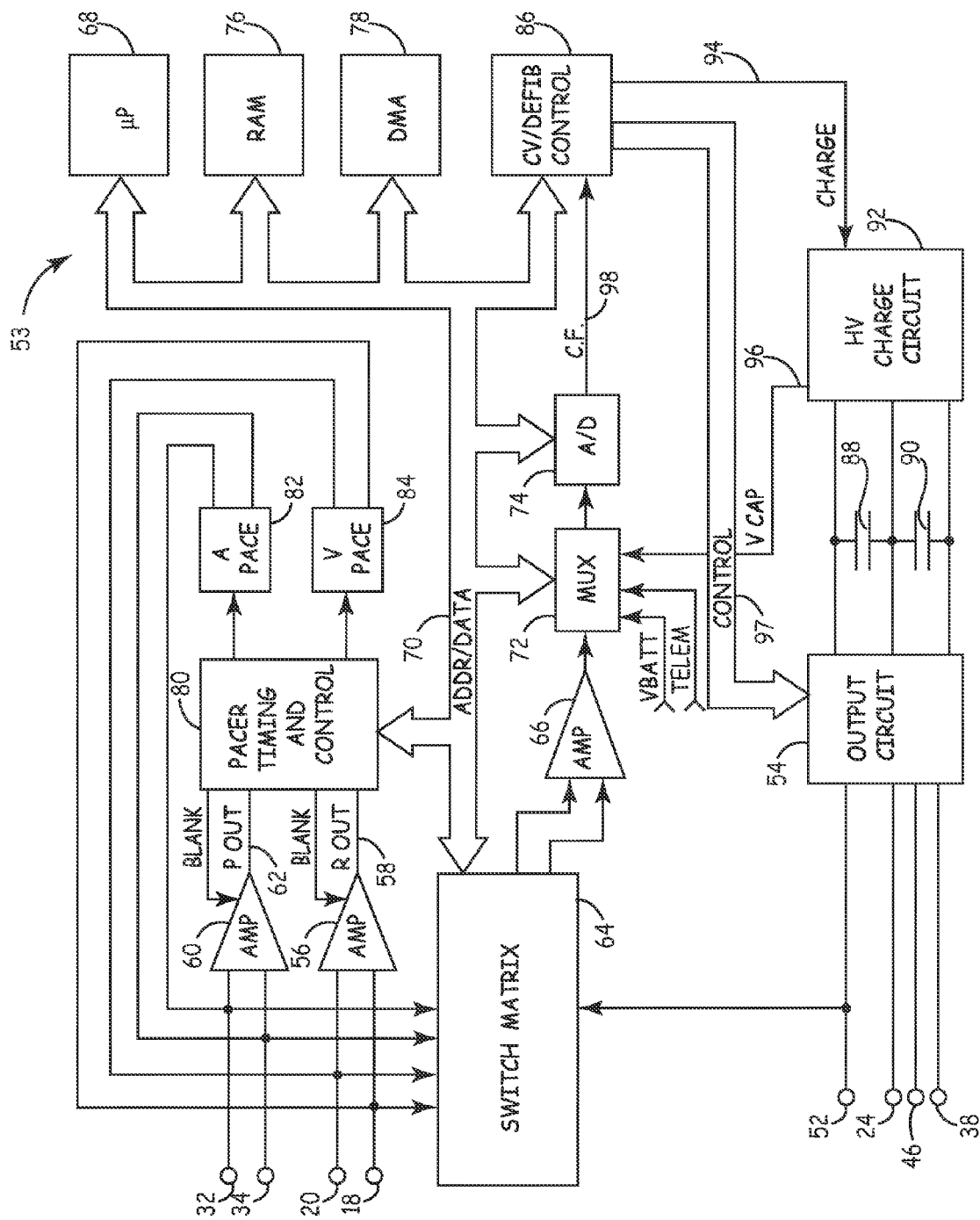
FIG. 2 is a functional schematic diagram illustrating a system capable of delivering anti-tachyarrhythmia therapies.

FIG. 2 is a functional schematic diagram illustrating a system 53 capable of delivering anti-tachyarrhythmia therapies such as ATP therapies, defibrillation, cardioversion, or a combination thereof. System 53 may further be capable of determining whether a tachyarrhythmia episode has terminated based on a relative decrease in tachyarrhythmia rate, a normalization of electrogram morphology criteria, or a combination thereof. The tachyarrhythmia may be atrial or ventricular. The system may be implemented within device 10 of FIG. 1, and may take the form of an implantable device that integrates various pacemaker/cardioverter/defibrillator functions. The diagrams of FIGS. 1 and 2 should be taken as exemplary of the type of device in which the invention may be embodied, however, and not as limiting of the invention as broadly embodied herein. For example, the invention may be practiced in a wide variety of device implementations, including devices providing therapies for treating atrial arrhythmias, ventricular arrhythmias, or both atrial and ventricular arrhythmias. In addition, the invention may be practiced in anti-tachycardia or anti-bradycardia pacemakers that do not provide cardioversion or defibrillation, as well as devices that deliver different forms of anti-arrhythmia therapies such as nerve stimulation or drug administration. Further, the invention may be practiced in devices that provide no therapy, but only provide monitoring capabilities.

In the example of FIG. 2, electrode 52 represents the uninsulated portion of the housing of device 10, i.e., the "can," which may function as a defibrillation electrode. Electrodes 24, 38, 46, and 52 are coupled to high voltage output circuit 54. Electrodes 18 and 20 are coupled to R-wave amplifier 56, which preferably takes the form of an automatic gain controlled amplifier providing an adjustable sensing threshold as a function of the measured R-wave amplitude. A signal is generated on R-out line 58 whenever the signal sensed between electrodes 18 and 20 exceeds the present sensing threshold.

Electrodes 32 and 34 are coupled to a P-wave amplifier 60, which also may take the form of an automatic gain controlled amplifier providing an adjustable sensing threshold as a function of the measured P-wave amplitude. A signal is generated on P-out line 62 when the signal sensed between electrodes 32 and 34 exceeds the sensing threshold. Switch matrix 64 selects which of the available electrodes are coupled to wide band amplifier 66 for use in digital signal analysis. Selection of electrodes is controlled by a controller, which may take the form of a microprocessor 68. Microprocessor 68 controls selection of electrodes by switch matrix 64 via data/address bus 70. Signals from the electrodes selected for coupling to bandpass amplifier 66 are provided to multiplexer 72 and thereafter converted to multi-bit digital signals by A/D converter 74, for storage in random access memory (RAM) 76 under control of direct memory access circuit 78.

Microprocessor 68 may employ digital signal analysis techniques to characterize the digitized signals stored in random access memory 76 to recognize and classify the heart rhythm using any of a variety of known signal processing methods. In particular, microprocessor 68 may implement a detector that tracks the cycle length and regularity of the heart rhythm during a tachyarrhythmia episode. For example, the detector may track a tachyarrhythmia rate of a patient and morphologies of cardiac waveforms to monitor the tachyarrhythmia episode. From the tachyarrhythmia rate, morphologies, or both, microprocessor 68 may, for example, detect the termination of an identified tachyarrhythmia episode. The remainder of the circuitry illustrated in FIG. 2 is dedicated to the provision of cardiac pacing, cardioversion, and defibrillation therapies.

Pacer timing/control circuitry 80 may include programmable digital counters that control the basic time intervals associated with DDD, VVI, DVI, VDD, AAI, DDI and other modes of single and dual chamber pacing well known to the art. More particularly, circuitry 80 is configured to control escape intervals associated with ATP in the atrium, the ventricle, or both the atrium and ventricle. To treat an episode of tachyarrhythmia, circuitry 80 may employ known ATP, defibrillation, or cardioversion therapies.

Intervals defined by pacing circuitry 80 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 68, in response to stored data in memory 76, and are communicated to the pacing circuitry 80 via address/data bus 70. Circuitry 80 also determines the amplitude of the cardiac pacing pulses under control of microprocessor 68.

During pacing, the escape interval counters within pacer timing/control circuitry 80 are reset upon sensing of R-waves and P-waves, and in accordance with the selected mode of pacing on time-out trigger generation of pacing pulses by pacer output circuits 82 and 84, which are coupled to electrodes 18, 20, 32, and 34. The escape interval counters are also reset upon generation of pacing pulses, and thereby control the basic timing of cardiac pacing functions, including anti-tachyarrhythmia pacing.

The durations of the intervals defined by the escape interval timers are determined by microprocessor 68 via data/address bus 70. The value of the count present in the escape interval counters when reset by sensed R-waves and P-waves may be used to measure the durations of R—R intervals, P—P intervals, P-R intervals and R-P intervals, also known as W intervals, M intervals, AV intervals, and VA intervals, respectively. An R—R interval, for example, is the length of time between a first ventricular event and a subsequent ventricular event. The resulting measurements can be stored in memory 76 and may be used to detect tachyarrhythmias. To detect tachycardia and associated cycle length and regularity, the invention may employ any of a variety of known tachycardia detection algorithms, e.g., comparison of the R—R interval to a tachycardia detection interval (TDI). Further, the durations above may be measured during a tachyarrhythmia episode and used alone or in conjunction with obtained electrogram morphologies to detect termination of the tachyarrhythmia episode.

In the event that a tachyarrhythmia episode is detected, and an anti-tachyarrhythmia pacing regimen is desired, microprocessor 68 prescribes appropriate timing intervals for controlling generation of ATP therapies by pacer timing and control circuitry 80. In particular, the timing intervals control the operation of the escape interval counters in circuitry 80 and define refractory periods during which detection of R-waves and P-waves are ineffective to restart the escape interval counters.

In operation, microprocessor 68 selects one of several ATP therapy sequences based on characteristics of the heart rhythm, such as cycle length and regularity. In the event that generation of a cardioversion or defibrillation shock is required, microprocessor 68 employs the escape interval counter to control timing of cardioversion and defibrillation shocks, as well as associated refractory periods.

In response to the detection of atrial or ventricular fibrillation or tachyarrhythmia requiring a cardioversion shock, microprocessor 68 activates cardioversion/defibrillation control circuitry 86, which initiates charging of the high voltage capacitors 88 and 90 via charging circuit 92, under control of high voltage charging control line 94. The voltage on high voltage capacitors 88, 90 is monitored via VCAP line 96, which is passed through multiplexer 72 and in response to reaching a predetermined value set by microprocessor 68, results in generation of a logic signal on Cap Full (CF) line 98, terminating charging.

Thereafter, timing of the delivery of the defibrillation or cardioversion shock is controlled by circuitry 86 via control bus 97. Microprocessor 68 may detect termination of the tachyarrhythmia episode during the charging of capacitors 88 and 90 or during a subsequent confirmation period after charging is completed, and abort delivery of the cardioversion shock in response to the detected termination. Following delivery of the fibrillation or tachycardia therapy, microprocessor 68 then returns device 10 to cardiac pacing and awaits the next pacing event or sensed atrial or ventricular depolarization.

Device 10 may be configured to apply an increasingly aggressive regimen of therapies. Upon initial detection of a tachyarrhythmia, a sequence of ATP therapies may be selected and delivered to a heart of the patient. The sequence defines an order of ATP therapies to be applied in attempts to terminate the tachyarrhythmia episode. The ATP therapies will typically be ordered from least to most aggressive. If the rate of the tachyarrhythmia episode increases following application of the first ATP therapy, microprocessor 68 controls circuitry 80 to apply the next ATP therapy in the sequence, i.e., a more aggressive therapy. If the rate of the tachyarrhythmia episode does not increase, microprocessor 68 determines whether the tachyarrhythmia episode terminates and continues applying therapies when the tachyarrhythmia episode is redetected.

Figure 3:
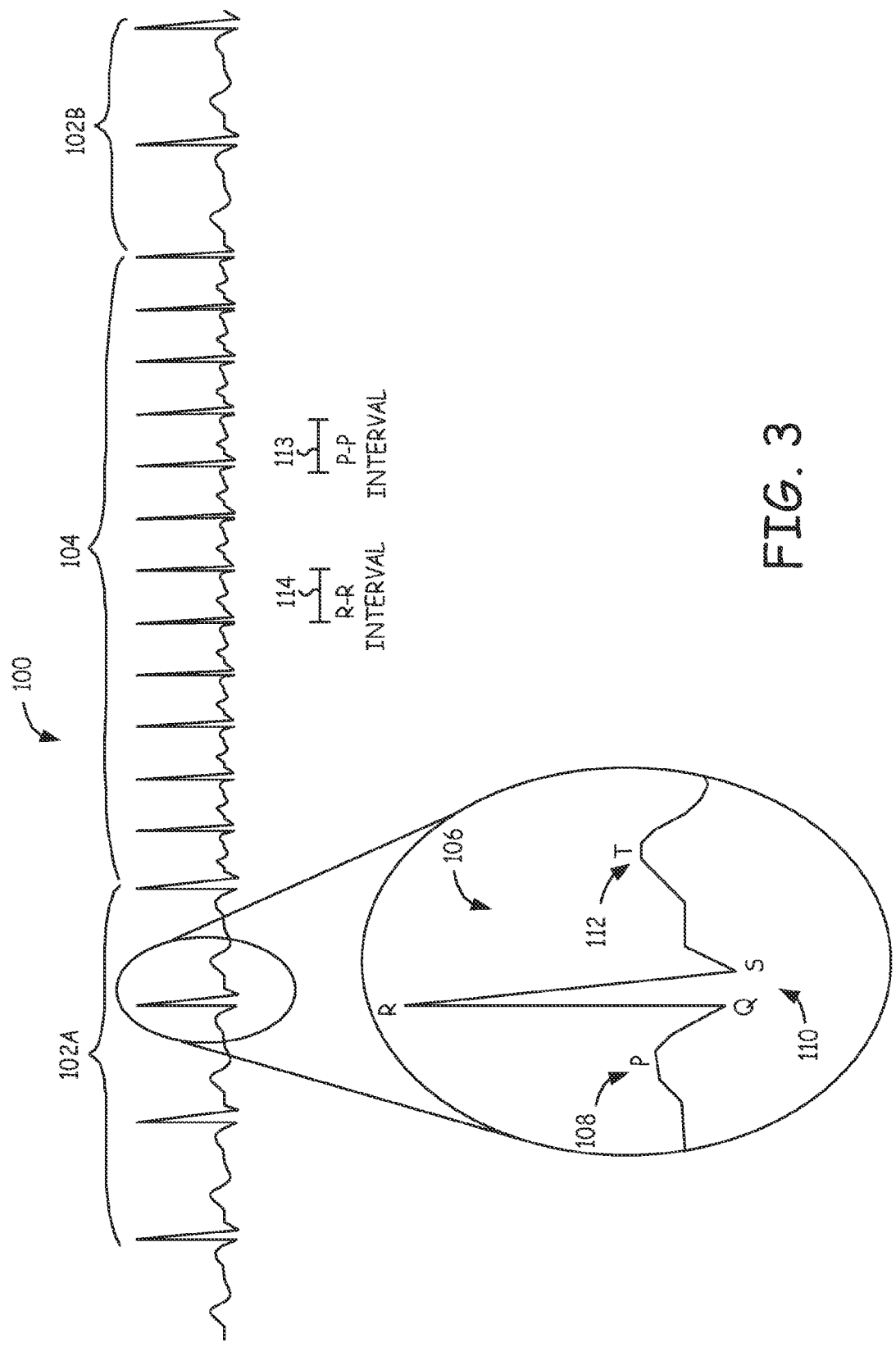
FIG. 3 is a schematic diagram illustrating an exemplary electrogram of a tachyarrhythmia episode.

FIG. 3 is a schematic diagram illustrating an exemplary electrogram 100 of a tachyarrhythmia episode. Electrogram 100 of FIG. 3 is for purposes of example. In operation, a medical device may use an electrogram, an electrocardiogram, or combination thereof in order to track a tachyarrhythmia episode. In electrogram 100 of FIG. 3, a heart rate of a patient goes from a normal sinus rhythm 102A into a tachyarrhythmia episode 104. Tachyarrhythmia episode 104 terminates, and the patient returns to normal sinus rhythm 102B. Although shown in FIG. 3 to spontaneously terminate, tachyarrhythmia episode 104 may terminate as a result of provided therapy. Tachyarrhythmia episode 104 may be a ventricular tachycardia episode, a supraventricular tachycardia episode, or a concomitant supraventricular and ventricular tachycardia, defined here as "double tachycardia".

While the patient is in sinus rhythm 102, microprocessor 68 may obtain a morphology of a cardiac waveform 106 associated with a "normal" heart beat. Cardiac waveform 106 may be defined by a series of peaks. In the example of FIG. 3, cardiac waveform 106 is defined by a P-wave 108 associated with an atrial depolarization, a QRS complex 110 that represents the time it takes for depolarization of ventricles of the heart, and a T-wave 112 associated with ventricular repolarization. The peaks associated with P-wave 108, QRS complex 110, and T-wave 112 each have a set of characteristics, such as an amplitude, a polarity, and a width that define the shape.

Microprocessor 68 may analyze the characteristics of P-wave 108, QRS complex 110, and T-wave 112 to generate a template morphology of cardiac waveform 106. Microprocessor 68 may compare the template morphology to morphologies of other cardiac waveforms and classify the morphologies as normal or abnormal. For example, a morphology may be compared to the template morphology and receive a score based on the similarities and differences in peak amplitudes, width, and polarity. When the score is above a threshold, the morphology may be classified as "normal." When the score is below a threshold, the score may be classified as "abnormal."

An implanted medical device, such as implanted medical device 10, may detect tachyarrhythmia episode 104 via any of a number of conventional detection algorithms. Implanted medical device 10 may be configured, for example, to detect a tachyarrhythmia episode when a heart rate of a patient exceeds a threshold heart rate, e.g., when the R—R interval is less than the TDI for a programmed duration. Upon detection of tachyarrhythmia episode 104, or at other times throughout the episode, implanted medical device 10 measures a metric of a tachyarrhythmia rate of tachyarrhythmia episode 104, such as a median of the tachyarrhythmia rate, a mean of the tachyarrhythmia rate, a maximum of the tachyarrhythmia rate, or a minimum of the tachyarrhythmia rate, and determines a relative threshold tachyarrhythmia rate. The relative threshold rate may, for example, be the metric of the tachyarrhythmia rate of the tachyarrhythmia episode 104.

Alternatively, the relative threshold rate may be the mean or median rate of the tachyarrhythmia episode minus an offset. The offset may be a defined value or may be calculated as a function of the metric of the rate of the tachyarrhythmia episode 104, the metric of the heart rate of sinus rhythm 102A, or combination thereof. In this manner, the threshold tachyarrhythmia rate is relative to the particular tachyarrhythmia episode experienced by the patient. Determining termination of a tachyarrhythmia episode based on a relative tachyarrhythmia rate increases the accuracy of determining whether an identified tachyarrhythmia episode has terminated.

During tachyarrhythmia episode 104, implanted medical device 10 may obtain a rate and a morphology of a cardiac waveform associated with the tachyarrhythmia episode. Implanted medical device 10 may obtain the tachyarrhythmia rate associated with the heart beat as durations between atrial depolarizations or durations between ventricular depolarizations, e.g., P—P intervals 113 or R—R intervals 114, respectively. Alternatively, obtaining the tachyarrhythmia rate associated with the heart beat may include measuring other atrial or ventricular intervals such as P-R intervals or R-P intervals.

Implanted medical device 10 determines whether tachyarrhythmia episode 104 has terminated based on the tachyarrhythmia rate and the morphology associated with the beat. The accuracy and sensitivity of detected terminations may further be improved by using both a relative tachyarrhythmia rate and a morphology of a cardiac waveform associated with the heart beat.

Figure 4:
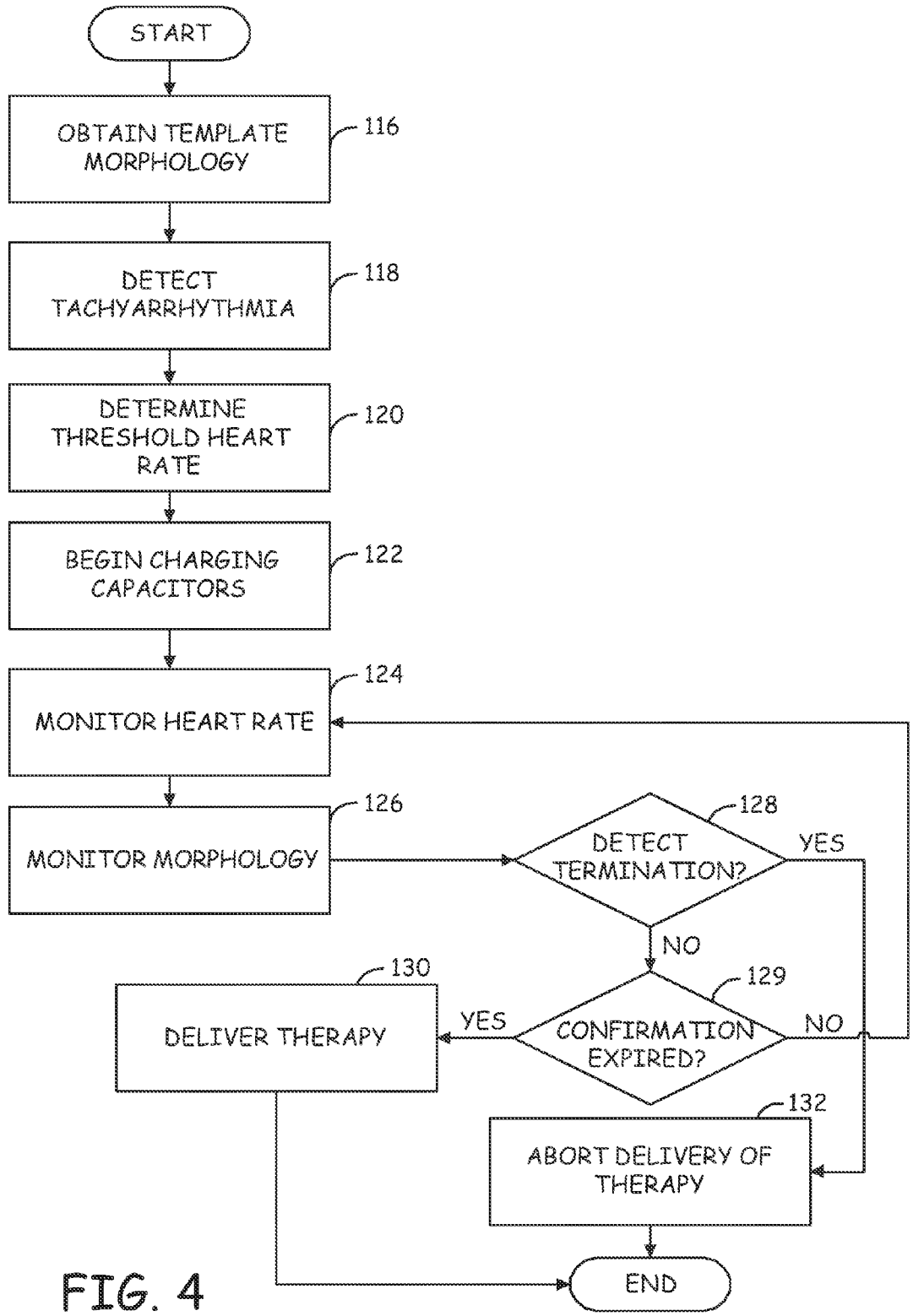
FIG. 4 is a flow diagram illustrating a technique for aborting a shock upon detecting termination of a tachyarrhythmia episode.

FIG. 4 is a flow diagram illustrating a technique for aborting a shock based on detecting termination of a tachyarrhythmia episode. A medical device, such as implanted medical device 10, obtains a morphology of a cardiac waveform while a patient is in sinus rhythm and analyzes the morphology to develop a template morphology (116).

Implanted medical device 10 detects a tachyarrhythmia episode (118). Implanted medical device 10 may detect the tachyarrhythmia episode via any of a number of conventional detection algorithms. Implanted medical device 10 may be configured, for example, to detect a tachyarrhythmia episode when a tachyarrhythmia rate of a patient exceeds a threshold tachyarrhythmia rate for a defined number of beats. The tachyarrhythmia rate may be determined according to a ventricular rate determined by an R—R interval, an atrial rate determined by an P—P interval, or similar interval.

Implanted medical device 10 determines a threshold tachyarrhythmia rate upon detection of the tachyarrhythmia episode or at other times throughout the episode (120). The threshold tachyarrhythmia rate may be a metric of the rate of the tachyarrhythmia episode, such as a median of the tachyarrhythmia rate, a mean of the tachyarrhythmia rate, a maximum of the tachyarrhythmia rate or a minimum of the tachyarrhythmia rate. Further, implanted medical device 10 may subtract an offset from the metric of the tachyarrhythmia rate of the tachyarrhythmia episode to obtain the threshold tachyarrhythmia rate. Alternatively, the threshold tachyarrhythmia rate may be a previously defined tachyarrhythmia rate.

Implanted medical device 10 begins charging capacitors 88 and 90 (122). The energy stored in capacitors 88 and 90 may be used to provide anti-tachycardia therapy such as a shock or a pulse to a heart of the patient.

During the charging period of capacitors 88 and 90 and/or during a subsequent confirmation period, implanted medical device 10 monitors a tachyarrhythmia rate associated with a heart beat during the tachyarrhythmia episode (124). Obtaining the tachyarrhythmia rate associated with the heart beat may include measuring an R—R interval. Alternatively, obtaining the tachyarrhythmia rate associated with the heart beat may include measuring other atrial or ventricular intervals, such as a P—P interval, a P-R interval, or an R-P interval.

Implanted medical device 10 may further monitor an electrogram morphology of a cardiac waveform associated with the heart beat of the patient (126). Implanted medical device 10 determines whether the tachyarrhythmia episode has terminated during a charging period of capacitors 88 and 90 and/or during a subsequent "confirmation period" after the charging is completed (128). The confirmation period aids in preventing inadvertent application of tachycardia therapy to the patient, which may cause significant patient discomfort. Implanted medical device 10 may determine termination of the tachyarrhythmia episode based on the tachyarrhythmia rate of the patient, the morphology of the cardiac waveform, or a combination thereof. For purposes of example, FIG. 4 illustrates the use of both tachyarrhythmia rate and morphology. For example, implanted medical device 10 may compare the measured R—R interval to a threshold R—R interval and the obtained morphology to the template morphology and determine whether the tachyarrhythmia episode has terminated based on the comparisons.

When implanted medical device 10 determines that the tachyarrhythmia episode has terminated, implanted medical device 10 aborts the anti-tachycardia therapy to be applied to the patient (132). Implanted medical device 10 may, for example, detect termination when the measured R—R interval is greater than the threshold R—R interval and, optionally, the obtained morphology substantially matches the template morphology.

When implanted medical device 10 determines that the tachyarrhythmia episode has not terminated throughout the charging of capacitors 88 and 90 and/or the subsequent confirmation period, implanted medical device 10 determines whether the charging period and the subsequent confirmation period has expired (129). When the charging period and the subsequent confirmation period has expired, implanted medical device 10 may apply the anti-tachycardia therapy, e.g., the shock or pulse, in attempts to terminate the tachyarrhythmia episode (130). When the charging period and the subsequent confirmation period has not expired, implanted medical device 10 continues to monitor the tachyarrhythmia rate and morphologies.

Figure 5:
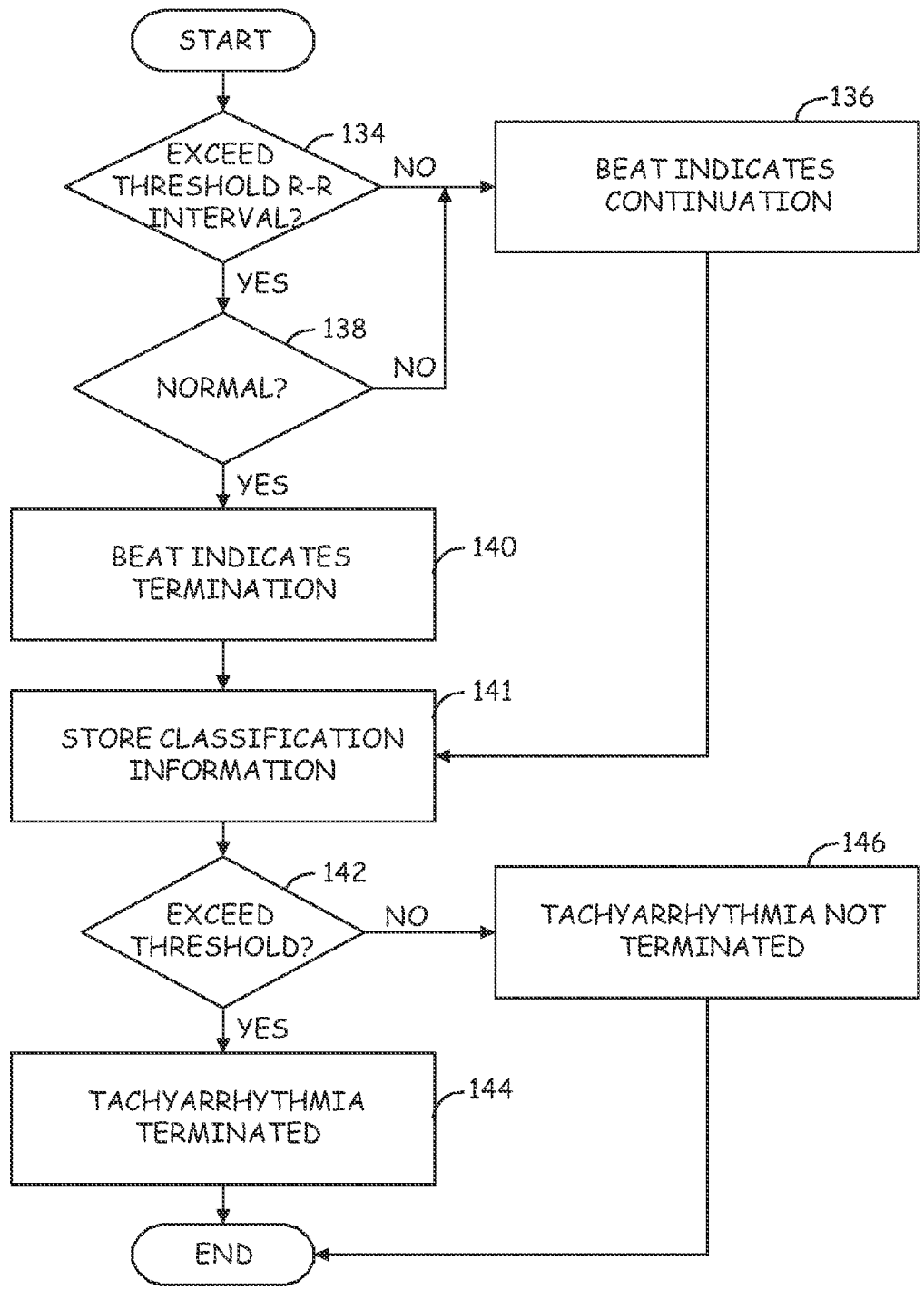
FIG. 5 is a flow diagram illustrating detection of termination of a tachyarrhythmia episode based a relative decrease in tachyarrhythmia rate and a normalization of electrogram morphology criteria.
Figure 6:
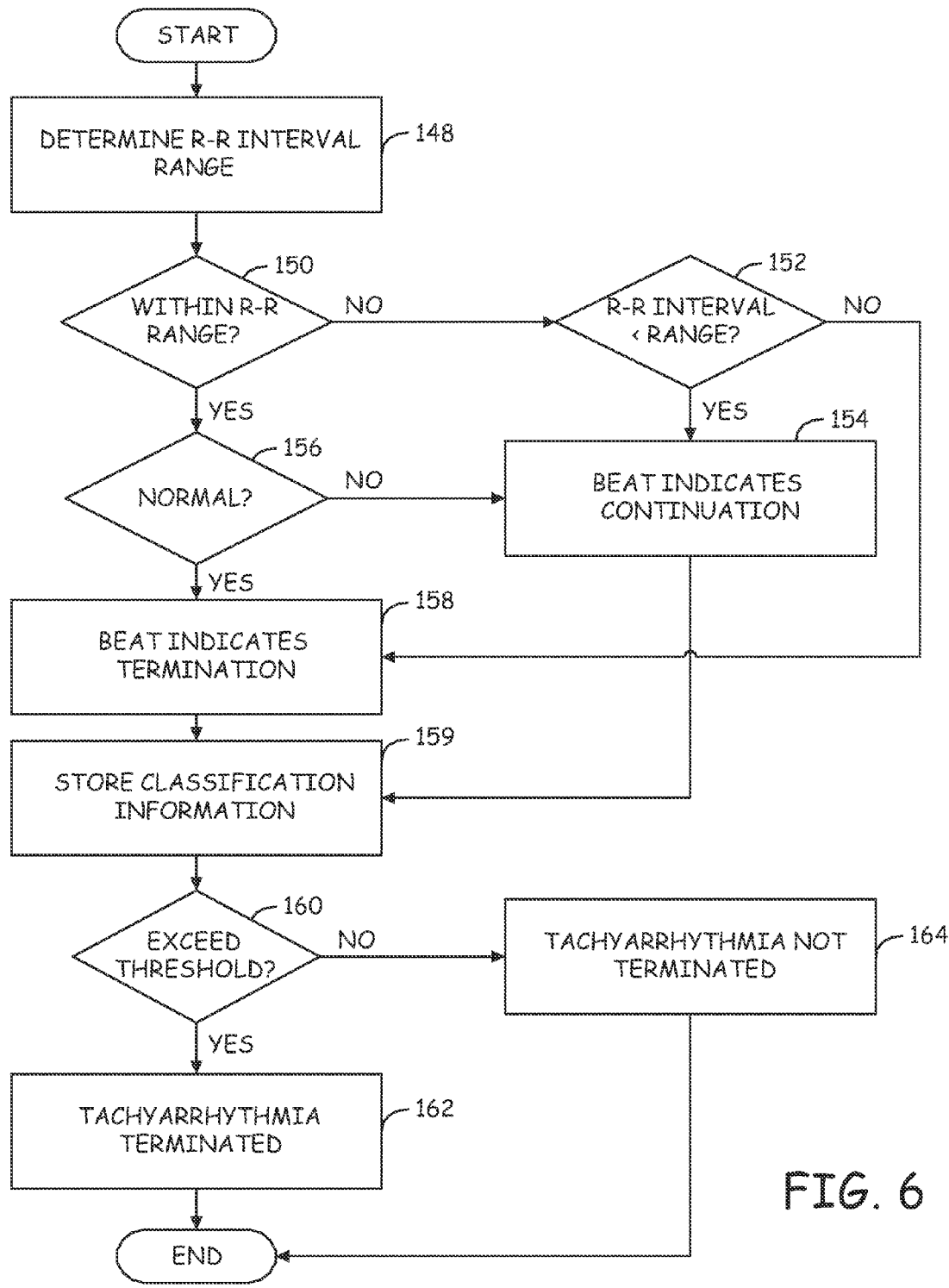
FIG. 6 is another flow diagram illustrating detection of termination of a tachyarrhythmia episode based on a relative decrease in tachyarrhythmia rate and a normalization of electrogram morphology criteria.

FIGS. 5 and 6 are flow diagrams illustrating techniques for determining termination of a tachyarrhythmia episode and may be viewed as an expansion of step 128 of FIG. 4. FIG. 5 is a flow diagram illustrating detection of termination of a tachyarrhythmia episode based on a relative decrease in tachyarrhythmia rate and a normalization of electrogram morphology criteria. Although termination of the tachyarrhythmia episode may be detected based on a relative decrease in tachyarrhythmia rate, a normalization of electrogram morphology criteria, or a combination thereof, for purposes of illustration, the termination detection technique of FIG. 5 is based on both a relative decrease in tachyarrhythmia rate and a normalization of electrogram morphology criteria. In other words, termination may be detected based on the relative decrease in tachyarrhythmia rate alone or, optionally, in combination with a normalization of the electrogram morphology criteria.

Implanted medical device 10 determines whether an R—R interval associated with a heart beat exceeds a threshold R—R interval (134). Although in the example of FIG. 5 the R—R interval is used as a measure of a tachyarrhythmia rate, any atrial or ventricular interval may be used as discussed above. The threshold R—R interval is relative to the particular tachyarrhythmia episode experienced by the patient. The threshold R—R interval may be a metric of a number of R—R intervals of the tachyarrhythmia episode. For example, the threshold R—R interval may be a mean or median of the first ten R—R intervals or a rolling median of the most recent ten R—R intervals of the tachyarrhythmia episode. Atrial episodes can be very long and the rate at detection can be very different than the rate later into the episode. For this reason, the use of a rolling median may be desirable for atrial tachyarrhythmia episodes.

Alternatively, the threshold R—R interval may be the mean or median of a number of R—R intervals plus an offset. For example, the threshold R—R interval may be the median of the first ten R—R intervals of the tachyarrhythmia episode plus fifty milliseconds. The threshold R—R interval may also be a defined value, such as 400 milliseconds. When the measured R—R interval is less than the threshold R—R interval, implanted medical device 10 classifies the beat as indicating continuation of the tachyarrhythmia episode (136) and stores the classification information (141).

When the measured R—R interval exceeds the threshold R—R interval, implanted medical device 10 compares an obtained morphology of the cardiac waveform associated with the beat to a template morphology to determine whether the obtained morphology categorizes as normal (138). When implanted medical device 10 categorizes the morphology as abnormal compared to the template morphology, implanted medical device 10 classifies the beat associated with the morphology as indicating continuation of the tachyarrhythmia episode (136) and stores the classification information (141).

When implanted medical device 10 categorizes the obtained morphology as normal compared to the template morphology, implanted medical device 10 classifies the beat associated with the morphology as indicating termination of the tachyarrhythmia episode (140) and stores the classification information (141). Implanted medical device 10 then determines whether a number of beats indicating termination of the tachyarrhythmia episode exceed a threshold (142). When the number of beats indicating termination of the tachyarrhythmia episode exceeds the threshold, implanted medical device 10 detects termination of the tachyarrhythmia episode (144). For example, implanted medical device 10 may consider the tachyarrhythmia episode terminated when four out of the last five beats indicate termination. Alternatively, a successive number of beats may need to indicate termination of the tachyarrhythmia episode in order to detect termination of the tachyarrhythmia episode. For instance, implanted medical device 10 may consider the tachyarrhythmia episode terminated when five consecutive beats indicate termination.

When the number of beats indicating termination of the tachyarrhythmia episode is less than the threshold or when implanted medical device 10 classifies a beat as indicating continuation of the tachyarrhythmia episode, i.e., based on the tachyarrhythmia rate, implanted medical device 10 determines that the tachyarrhythmia episode has not terminated (146).

FIG. 6 is another flow diagram illustrating detection of termination of a tachyarrhythmia episode based a relative decrease in tachyarrhythmia rate and a normalization of electrogram morphology criteria. Again, although termination of the tachyarrhythmia episode may be detected based on a relative decrease in tachyarrhythmia rate, a normalization of electrogram morphology criteria, or a combination thereof, for purposes of illustration, the termination detection technique of FIG. 6 is based on both a relative decrease in tachyarrhythmia rate and a normalization of electrogram morphology criteria.

Implanted medical device 10 determines a range of R—R intervals (148). Although in the example of FIG. 6 the R—R interval is used as a measure of a tachyarrhythmia rate, any atrial or ventricular interval may be used as discussed above. Implanted medical device 10 may calculate, for example, a metric of a number of R—R intervals of the tachyarrhythmia episode and identify a range using the calculated metric of the R—R intervals. For instance, the R—R interval range may extend from a mean or median R—R interval value plus sixty milliseconds to a mean or median R—R interval plus one hundred milliseconds. In this manner, the R—R interval range is relative to each tachyarrhythmia episode. Alternatively, the R—R interval range may be defined, in which case, the range is common to all tachyarrhythmia episodes.

Implanted medical device 10 determines whether an R—R interval associated with a heart beat is within the R—R interval range (150). When the R—R interval is outside of the R—R interval range, implanted medical device 10 determines whether the R—R interval falls below the R—R interval range (152). When the R—R interval falls below the R—R interval range, implanted medical device 10 classifies the beat associated with the R—R interval as indicating continuation of the tachyarrhythmia episode (154) and stores the classification information (159).

When the R—R interval is within the R—R interval range, implanted medical device 10 compares a morphology of a cardiac waveform associated with the beat to a template morphology to determine whether the obtained morphology categorizes as normal (156). When implanted medical device 10 categorizes the morphology as abnormal, implanted medical device 10 classifies the beat as indicating continuation of the tachyarrhythmia episode (154) and stores the classification information (159).

When implanted medical device 10 categorizes the morphology as normal, implanted medical device 10 classifies the beat as indicating termination of the tachyarrhythmia episode (158) and stores the classification information (159). Implanted medical device 10 then determines whether a number of beats indicating termination of the tachyarrhythmia episode exceed a threshold (160). When the number of beats indicating termination of the tachyarrhythmia episode exceeds the threshold, implanted medical device 10 detects termination of the tachyarrhythmia episode (162).

When the number of beats indicating termination of the tachyarrhythmia episode is less than the threshold, implanted medical device 10 classifies the tachyarrhythmia episode as not terminated (164).

Figure 7:
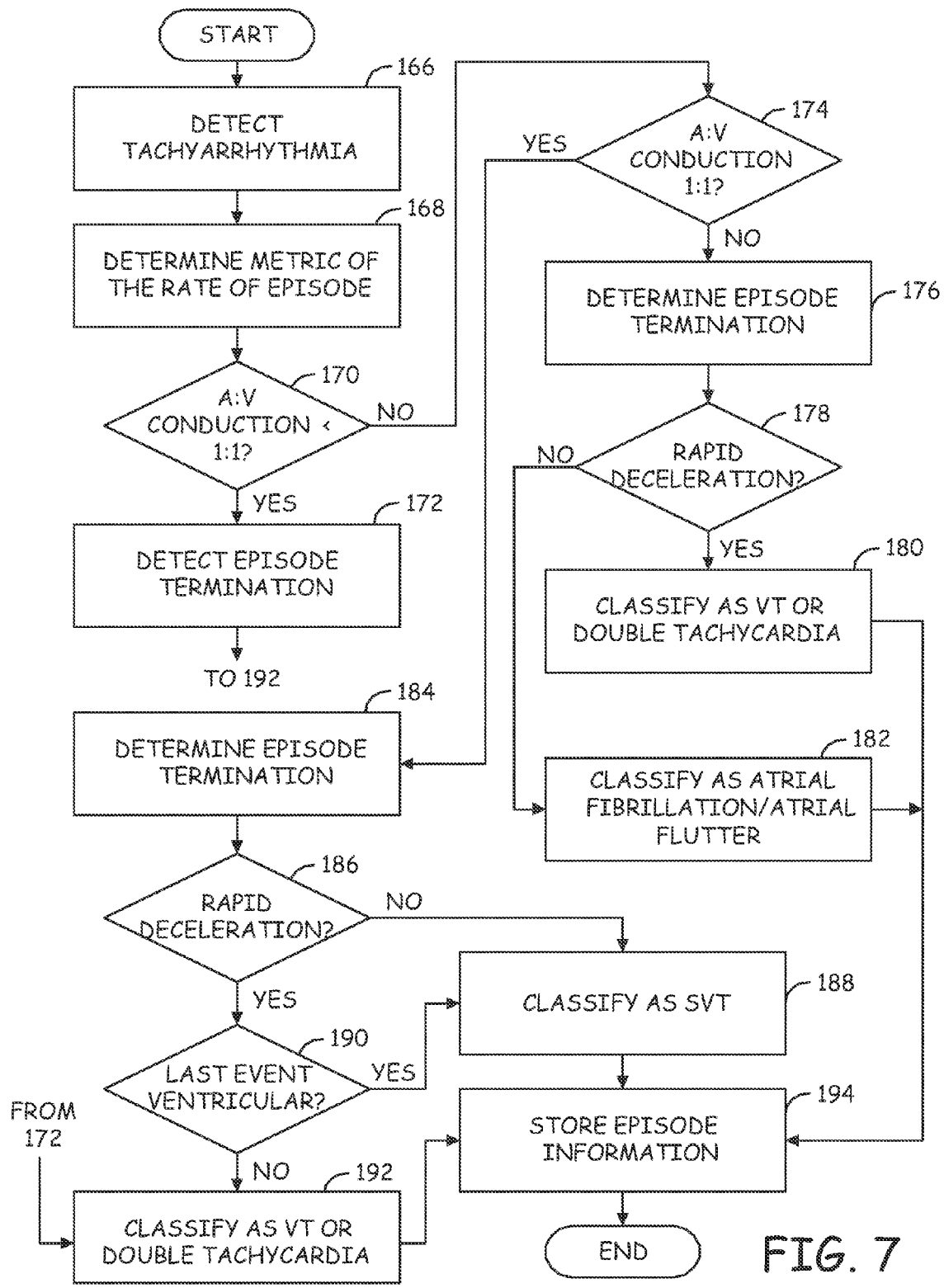
FIG. 7 is a flow diagram illustrating a technique for classifying a tachyarrhythmia episode based on information obtained at termination of the episode.

FIG. 7 is a flow diagram illustrating a technique for classifying the type of a tachyarrhythmia episode based on information obtained at a spontaneous termination of the episode. The technique illustrated by FIG. 7 is directed to cases of ventricular tachyarrhythmia for purposes example. In other embodiments, however, the invention may be applied to atrial tachyarrhythmia. A medical device, such as implanted medical device 10, detects a tachyarrhythmia episode (166). Implanted medical device 10 tracks ventricular and atrial events to determine a metric of a tachyarrhythmia rate of the tachyarrhythmia episode (168). For example, implanted medical device 10 may calculate a mean tachyarrhythmia rate of the tachyarrhythmia episode, a median tachyarrhythmia rate of the tachyarrhythmia episode, a maximum of the tachyarrhythmia rate, a minimum of the tachyarrhythmia rate, or similar metric of the tachyarrhythmia rate.

Implanted medical device 10 determines whether the tachyarrhythmia episode has an atrial to ventricular (A:V) conduction ratio that is less than 1:1 (170). When the A:V conduction ratio of the tachyarrhythmia episode is less than 1:1, implanted medical device 10 waits to detect episode termination (172) and classifies the tachyarrhythmia episode as a ventricular tachycardia (VT) or double tachycardia (192). Implanted medical device 10 may detect termination of the tachyarrhythmia episode based on an absolute or relative decrease in tachyarrhythmia rate, a normalization of electrogram morphology criteria, or a combination thereof.

When the A:V conduction ratio is greater than 1:1, implanted medical device 10 waits to detect episode termination (174, 176). After detecting episode termination, implanted medical device 10 determines whether the rate of the tachyarrhythmia episode rapidly decelerates at termination (178). For example, implanted medical device 10 may determine a metric of deceleration, such as a difference between two consecutive R—R intervals being larger than a threshold. Other metrics of deceleration may also be used. For example, the metric of deceleration may include the difference between two median heart rates or two mean heart rates. When the tachyarrhythmia episode rapidly decelerates, implanted medical device 10 classifies the tachyarrhythmia episode as a ventricular tachycardia (VT) or a double tachycardia (180). When the tachyarrhythmia episode does not rapidly decelerate, implanted medical device 10 classifies the tachyarrhythmia episode as atrial fibrillation or atrial flutter (182).

When the A:V conduction ratio is 1:1, implanted medical device 10 waits to detect episode termination (174,184) and determines whether the rate of the tachyarrhythmia episode rapidly decelerates at termination (186). When the tachyarrhythmia episode does not rapidly decelerate, implanted medical device 10 classifies the tachyarrhythmia episode as a supraventricular tachycardia (SVT) (188).

When the tachyarrhythmia episode rapidly decelerates, implanted medical device 10 determines from the tracked ventricular and atrial events whether a last event prior to the deceleration was a ventricular event (190). When the last event prior to the deceleration was a ventricular event, implanted medical device 10 classifies the tachyarrhythmia episode as a supraventricular tachycardia (SVT) (188). When the last event prior to the deceleration was not a ventricular event, i.e., was an atrial event, implanted medical device 10 classifies the tachyarrhythmia episode as a ventricular tachycardia (VT) or a double tachycardia (192).

Implanted medical device 10 stores tachyarrhythmia episode information upon classifying the tachyarrhythmia episode (194). Tachyarrhythmia episode information may include, for example, the type of tachyarrhythmia episode, the threshold tachyarrhythmia rate of the patient, atrial and ventricular events during the tachyarrhythmia episode, the morphologies obtained during the tachyarrhythmia episode, and the like. In some embodiments, implanted medical device 10 may conserve memory by storing certain classes of tachyarrhythmia episodes.

Figure 8:
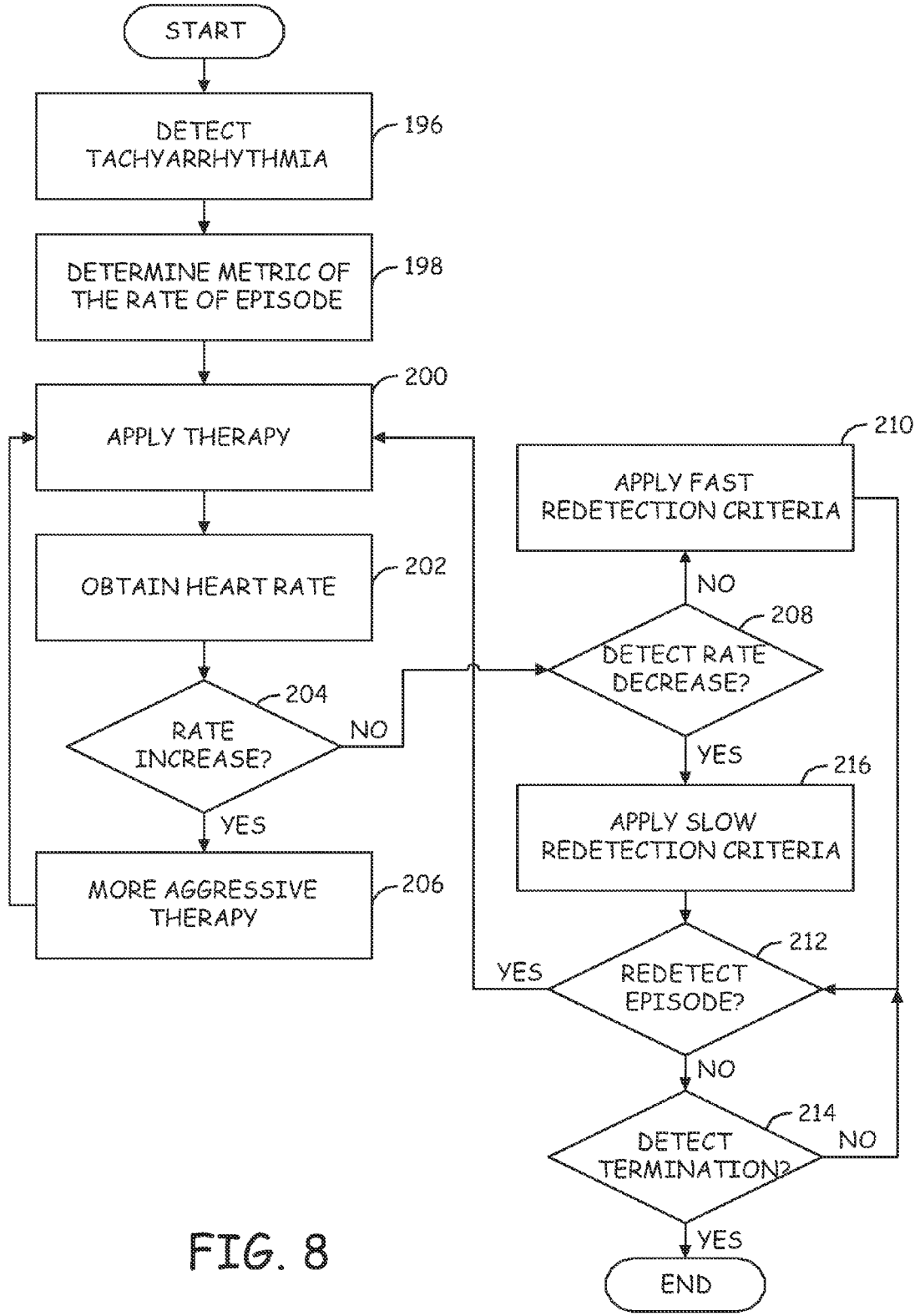
FIG. 8 is a flow diagram illustrating a technique for providing therapy to a tachyarrhythmia episode based on a heart rate of the tachyarrhythmia episode and a morphology of a cardiac waveform.

FIG. 8 is a flow diagram illustrating a technique for providing therapy to treat a tachyarrhythmia episode based on a rate of the tachyarrhythmia episode and optionally a morphology of a cardiac waveform. The technique illustrated by FIG. 8 is directed to cases of ventricular tachyarrhythmia for purposes example. In other embodiments, however, the invention may be applied to atrial tachyarrhythmia. A medical device, such as implanted medical device 10, detects a tachyarrhythmia episode (196). Implanted medical device 10 tracks ventricular and atrial events to determine a metric of a rate of the tachyarrhythmia episode (198). Implanted medical device 10 applies a therapy in an attempt to terminate the tachyarrhythmia episode (200).

After applying a therapy, implanted medical device 10 determines a rate of the current rhythm (202). Implanted medical device 10 may, for example, determine the tachyarrhythmia rate from the tracked atrial and ventricular events. For instance, the rate of the tachyarrhythmia episode may be a metric of a series of measured R—R intervals, P—P intervals, or the like. Implanted medical device 10 determines whether the rate of the tachyarrhythmia episode increased (204). When heart the rate of the tachyarrhythmia episode increases, implanted medical device 10 may select a more aggressive therapy, such as cardioversion or defibrillation, and apply the more aggressive therapy (206, 200).

When the rate of the tachyarrhythmia episode does not increase, implanted medical device 10 determines whether the rate of the tachyarrhythmia episode decreased (208). When the rate of the tachyarrhythmia episode does not decrease, implanted medical device 10 applies fast redetection criteria in attempts to redetect the tachyarrhythmia episode (210, 212). The fast redetection criteria may include comparing the rate of the tachyarrhythmia episode to a relative threshold tachyarrhythmia rate, e.g., over a range of 6 to 12 beats. When implanted medical device 10 redetects the tachyarrhythmia episode, implanted medical device 10 applies another therapy (200). When implanted medical device 10 does not redetect the tachyarrhythmia episode, implanted medical device 10 determines whether the tachyarrhythmia episode has terminated (214). When the tachyarrhythmia episode has not terminated, implanted medical device 10 reapplies the fast redetection criteria.

When the rate of the tachyarrhythmia episode decreases, implanted medical device 10 applies slow redetection criteria in attempts to redetect the tachyarrhythmia episode (216, 212). The slow redetection criteria may include comparing the rate of the tachyarrhythmia episode to a threshold tachyarrhythmia rate, comparing the pattern of atrial and ventricular depolarization events to known patterns of VT or SVT rhythms, and/or also comparing a morphology of a cardiac waveform associated with a heart beat with a template morphology. The slow detection criteria may be applied within an extended range, e.g., 18 to 60 beats. When implanted medical device 10 redetects the tachyarrhythmia episode, implanted medical device 10 applies another therapy (200). When implanted medical device 10 does not redetect the tachyarrhythmia episode, implanted medical device 10 determines whether the tachyarrhythmia episode has terminated (214). When the tachyarrhythmia episode has not terminated, implanted medical device 10 reapplies the slow redetection criteria.

Various embodiments of the invention have been described. These and other embodiments are within the scope of the following claims.

What is claimed is:

1. A method comprising:
   obtaining a cardiac tachyarrhythmia rate associated with a heart beat;
   obtaining a morphology of a cardiac waveform associated with the heart beat;
   determining whether a detected tachyarrhythmia episode has terminated based on the tachyarrhythmia rate and the morphology;
   classifying the arrhythmia type of the tachyarrhythmia episode based on information associated with the tachyarrhythmia episode at termination.

2. The method of claim 1, further comprising:
   classifying the beat as indicating termination of the tachyarrhythmia episode; and
   determining that the detected tachyarrhythmia episode has terminated when a number of beats classified as indicating termination of the tachyarrhythmia episode exceed a threshold.

3. The method of claim 2, wherein the threshold includes a number of consecutive beats.

4. The method of claim 2, wherein the threshold includes a portion of consecutive beats.

5. The method of claim 2, further comprising:
   comparing the tachyarrhythmia rate with a threshold tachyarrhythmia rate;
   comparing the morphology of the cardiac waveform with a template morphology of a cardiac waveform; and
   classifying the beat as indicating termination of the tachyarrhythmia episode when the tachyarrhythmia rate fails below the threshold tachyarrhythmia rate and the morphology categorizes as normal.

6. The method of claim 5, further comprising obtaining the template morphology during a sinus rhythm.

7. The method of claim 5, further comprising:
   measuring a metric of the tachyarrhythmia rate of the tachyarrhythmia episode; and
   calculating the threshold tachyarrhythmia rate as a function of the metric of the tachyarrhythmia rate.

8. The method of claim 7, wherein calculating the threshold tachyarrhythmia rate as a function of the metric of the tachyarrhnia rate includes subtracting an offset from the mefric of the rate of the tachyarrhythmia episode to calculate the threshold tachyarrhythmia rate.

9. The method of claim 7, wherein the metric of the tachyarrhythmia rate includes one of a median of the tachyarrhythmia rate, a mean of the tachyarrhythmia rate, a maximum of the tachyarrhythmia rate and a minimum of the tachyarrhythmia rate.

10. The method of claim 2, further comprising:
comparing the tachyarrhythmia rate with a range; and
classifying the beat as indicating termination of the tachyarrhythmia episode when the tachyarrhythmia rate fails below the range.

11. The method of claim 10, further comprising:
comparing the morphology with a template morphology when the tachyarrhythmia rate is within the range; and
classifying the beat as indicating termination of the tachyarrhythmia episode when the morphology categorizes as normal.

12. The method of claim 1, further comprising aborting delivery of therapy upon determining that the detected tachyarrhythmia episode has terminated.

13. The method of claim 1, further comprising:
identifying the tachyarrhythmia episode to have a 1:1 atrial to ventricular conduction rate;
identifying a rapid deceleration in the heart rate at termination of the tachyarrhythmia episode;
determining whether a last depolarization prior to the deceleration is a ventricular depolarization; and
classifying the arrhythmia type of the tachyarrhythmia episode as a supraventricular tachycardia when the last depolarization prior to the deceleration is a ventricular depolarization.

14. The method of claim 13, further comprising classifying the arrhythmia type of the tachyarrhythmia episode as a ventricular tachycardia when the last depolarization prior to the deceleration is not a ventricular depolarization.

15. The method of claim 1, further comprising:
applying a therapy to a patient
redetecting the tachyarrhythmia episode after applying the therapy; and
reapplying the therapy to the patient when the tachyarrhythmia episode is redetected.

16. The method of claim 15, wherein redetecting the tachyarrhythmia episode includes:
determining that a tachyarrhythmia rate of a successive heart beat does not decrease;
comparing the tachyarrhythmia rate of the successive heart beat to a threshold tachyarrhythmia rate; and
redetecting the tachyarrhythmia episode when the tachyarrhythmia rate of the successive heart beat exceeds the threshold.

17. The method of claim 15, wherein redetecting the tachyarrhythmia episode includes:
determining that a tachyarrhythmia rate of a successive heart beat decreases;
comparing the tachyarrhythmia rate of the successive heart beat to a threshold tachyarrhythmia rate;
comparing a morphology of the successive heart beat to a template morphology; and
redetecting the tachyarrhythmia episode when the tachyarrhythmia rate of the successive heart beat exceeds the threshold and the morphology of the successive heart beat categorizes as normal.

18. The method of claim 1, wherein obtaining a tachyarrhythmia rate associated with a heart beat includes obtaining an R—R interval associated with the heart beat.

19. A device comprising:
a first detector to detect a tachyarrhythmia rate associated with a heart beat;
a second detector to detect a morphology of a cardiac waveform associated with the heart beat; and
a processor to determine whether a detected tachyarrhythmia episode has terminated based on the tachyarrhythmia rate and the morphology, wherein the processor classifies the beat as indicating termination of the tachyarrhythmia episode and determines that the detected tachyarrhythmia episode has terminated when a number of beats classified as indicating termination of the tachvarrhvthmia episode exceed a threshold, and wherein the processor classifies the arrhythmia type of the tachyarrhythmia episode based on information associated with the tachyarrhythmia episode at termination.

20. The device of claim 19, wherein the threshold includes a number of consecutive beats.

21. The device of claim 19, wherein the threshold includes a portion of consecutive beats.

22. The device of claim 19, wherein the processor compares the tachyarrhythmia rate with a threshold tachyarrhythmia rate, compares the morphology of the cardiac waveform with a template morphology of a cardiac waveform, and classifies the beat as indicating termination of the tachyarrhythmia episode when the tachyarrhythmla rate is less than the threshold tachyarrhythmia rate and the morphology categorizes as normal.

23. The device of claim 22, wherein the processor compares the tachyantythmia rate with a range, and classifies the beat as indicating termination of the tachyarrhythmia episode when the tachyarrhythmia rate falls below the range.

24. The device of claim 23, wherein the processor compares the morphology with a template morphology when the tachyarrhythmia rate is within the range and classifies the beat as indicating termination of the tachyarrhythmia episode when the morphology categorizes as normal.

25. The device of claim 19, wherein the processor determines whether the taohyarrhythmia episode has terminated when a tachyarrhythmia rate of a successive beat decreases in response to delivered therapy and aborts the therapy when the tachyarrhythmia episode has terminated.

26. A device comprising:
a first detector to detect a tachyarrhythmia rate associated with a heart beat;
a second detector to detect a morphology of a cardiac waveform associated with the heart beat; and
a processor to determine whether a detected tachyarrhythmia episode has terminated based on the tachyarrhythmia rate and the morphology, wherein the processor classifies the beat as indicating termination of the tachyarrhythmia episode and determines that the detected tachyarrhythmia episode has terminated when a number of beats classified as indicating termination of the tachyarrhythmia episode exceed a threshold, and wherein the processor compares the tachyarrhythmia rate with a threshold tachyarrhythmia rate, compares the morphology of the cardiac waveform with a template morphology of a cardiac waveform, and classifies the beat as indicating termination of the tachyarrhythmia episode when the tachyarrhvthmia rate is less than the threshold tachyarrhythmia rate and the morphology categorizes as normal, wherein the processor measures a metric of the tachyarrhythmia rate of the tachyarrhythmia episode and subtracts from the metric of the tachyarrhythmia rate an offset to obtain the threshold tachyarrhythmia rate.

27. The device of claim 26, wherein the metric of the tachyarrhythmia rate includes one of a median of the tachyarrhythmia rate, a mean of the tachyarrhythmia rate, a maximum of the tachyarrhythmia rate and a minimum of the tachyarrhythmia rate.

28. A method comprising: measuring a metric of a rate of a tachyarrhythmia episode of the tachyarrhythmia episode;
calculating a relative threshold tachyarrhythmia rate as a function of the metric of the rate of the tachyarrhythmia episode;
comparing a tachyarrythmia rate associated with a heart beat with the relative threshold tachyarrhythmia rate; and
determining whether the detected tachyarrhythmia episode has terminated based on the comparison.

29. The method of claim 28, further comprising:
classifying the beat as indicating termination of the tachyarrhythmia episode when the tachyan-hythmia rate falls below the threshold tachyarrhythmia rate; and
determining that tile detected tachyarrhythmia episode has terminated when a number of beats classified as indicating termination of the tachyarrhythmia episode exceed a threshold.

30. The method of claim 28, wherein calculating the threshold tachyarrhythmia rate as a function of the metric of the tachyarrhythmia rate includes subtracting an offset from the metric of the rate of the tachyarrhythmia episode to calculate the threshold tachyarrhythmia rate.

31. The method of claim 28, wherein the metric of the tachyarrhythmia rate includes one of a median of the tachyarrhythmia rate, a mean of the tachyarrhythmia rate, a maximum of the tachyarrhythmia rate and a minimum of the tachyarrhythmia rate.

32. The method of claim 28, further comprising obtaining a tachyarrhythmia rate associated with a heart beat.

33. The method of claim 32, wherein obtaining a tachyarrhythmia rate associated with a heart beat includes obtaining an R—R interval associated with the heart beat.

34. The method of claim 28 further comprising:
determining termination of the tachyarrhythmia episode; and
classifying the arrhythmia type of the tachyarrhythmia episode based on information associated with the tachyarrhythmia episode at termination.

* * * * *

UNITED STATES PATENT AND TRADEMARK OFFICE
CERTIFICATE OF CORRECTION

PATENT NO.       : 7,103,404 B2
APPLICATION NO.  : 10/375457
DATED            : September 5, 2006
INVENTOR(S)      : Stadler et al.

It is certified that error appears in the above-identified patent and that said Letters Patent is hereby corrected as shown below:

Column 14, line 54, please delete "fails below" and insert --falls below--

Column 14, line 65, please delete "tachyarrhythrnia" and insert --tachyarrhythmia--

Column 15, line 10, please delete "fails below" and insert --falls below--

Column 16, line 10, please delete "tachvarrhvthmia" and insert --tachyarrhythmia--

Column 16, line 24, please delete "tachyarrhythmla" and insert --tachyarrhythmia--

Column 16, line 59, please delete "tachyarrhvthmia" and insert --tachyarrhythmia--

Column 16, line 28, please delete "tachyantythmia" and insert --tachyarrhythmia--

Column 16, line 37, please delete "taohyarrhythmia" and insert --tachyarrhythmia--

Column 17, line 9, please delete "tachyarrythmia" and insert --tachyarrhythmia--

Column 17, line 16, please delete "tachyan-hythmia" and insert --tachyarrhythmia--

Signed and Sealed this

Fifth Day of June, 2007

JON W. DUDAS
*Director of the United States Patent and Trademark Office*